US008362254B2

(12) United States Patent
Haremza et al.

(10) Patent No.: US 8,362,254 B2
(45) Date of Patent: Jan. 29, 2013

(54) METHOD FOR THE PRODUCTION OF 4-FORMYLAMINOPIPERIDINE DERIVATIVES

(75) Inventors: Sylke Haremza, Neckargemuend (DE); Thomas Berg, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 693 days.

(21) Appl. No.: 12/600,303

(22) PCT Filed: May 28, 2008

(86) PCT No.: PCT/EP2008/056550

§ 371 (c)(1), (2), (4) Date: Nov. 16, 2009

(87) PCT Pub. No.: WO2008/145673

PCT Pub. Date: Dec. 4, 2008

(65) Prior Publication Data

US 2010/0160637 A1 Jun. 24, 2010

(30) Foreign Application Priority Data

May 31, 2007 (EP) .................................... 07109320

(51) Int. Cl.
*A01N 43/40* (2006.01)
*C07D 211/30* (2006.01)

(52) U.S. Cl. ........................................ 546/190; 514/316

(58) Field of Classification Search .................. 546/190; 514/316

See application file for complete search history.

(56) References Cited

U.S. PATENT DOCUMENTS

| | | | |
|---|---|---|---|
| 3,347,916 | A | 10/1967 | Huber |
| 4,331,586 | A | 5/1982 | Hardy |
| 4,605,743 | A | 8/1986 | Malz, Jr. et al. |
| 4,789,757 | A | 12/1988 | Carter |
| 4,976,889 | A | 12/1990 | Aumueller et al. |

FOREIGN PATENT DOCUMENTS

| | | |
|---|---|---|
| DE | 230 527 | 12/1985 |
| EP | 0 302 020 | 2/1989 |
| EP | 0 316 582 | 5/1989 |
| EP | 0 508 940 | 10/1992 |
| JP | 07304737 | 11/1995 |

OTHER PUBLICATIONS

Takahashi, Kyoko et al, "Formylation of Amines by Dimethylformamide in the Presence of Hydrous Zirconium Oxide", Agric. Biol. Chem., vol. 52, No. 3, pp. 853-854, (1988).

U.S. Appl. No. 12/160,724, filed Jul. 11, 2008, Schambony, et al.

*Primary Examiner* — Janet Andres
*Assistant Examiner* — John Mabry
(74) *Attorney, Agent, or Firm* — Oblon, Spivak, McClelland, Maier & Neustadt, L.L.P.

(57) ABSTRACT

Method for producing 4-formylaminopiperidine derivatives of the formula (I)

(I)

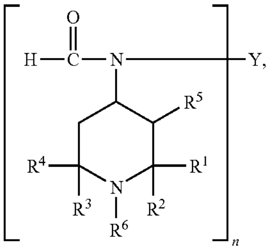

and also the acid addition salts of these compounds, comprising the reaction of 4-aminopiperidine derivatives of the formula (II) or the acid addition salts of these compounds (II)

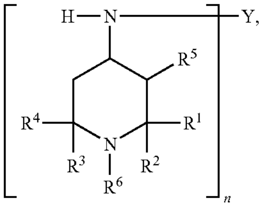

in the presence of compounds of the formula (III)

(III)

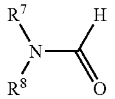

and the use of 4-formylaminopiperidine derivatives of the formula (I) produced in such a way for protecting inanimate organic material against the effect of light.

18 Claims, No Drawings

METHOD FOR THE PRODUCTION OF 4-FORMYLAMINOPIPERIDINE DERIVATIVES

The present invention relates to methods for producing 4-formylaminopiperidine derivatives. Furthermore, the invention relates to methods for isolating and working up 4-formylaminopiperidine derivatives. In addition, the invention relates to the use of the 4-formylaminopiperidine derivatives for the protection of inanimate organic material against the effect of light. Further embodiments of the present invention can be found in the claims, the description and the examples. It goes without saying that the features of the subject matter according to the invention specified above and yet to be described below can be used not only in the combination specifically stated in each case, but also in other combinations, without departing from the scope of the invention.

It is known that 4-formylaminopiperidine derivatives (4-N-formylated 4-aminopiperidine derivatives) are produced by reacting 4-aminopiperidine derivatives with formic acid or formic acid esters. EP 0 316 582 A1 discloses in particular the use of methyl or ethyl esters of formic acid. Corresponding to EP 0 316 582 A1, it is possible to work with or without catalyst in the methods. Catalysts specified in EP 0 316 582 A1 are Lewis acids, in particular titanium orthoesters and specifically titanium orthobutylate.

4-Formylaminopiperidine derivatives, such as, for example, 4-amino-2,2,6,6-tetraalkylpiperidine derivatives, are used, as described in EP 0 316 582 A1, as photostabilizers for polymers.

U.S. Pat. No. 4,789,757-A discloses the N-formylation of amino acids. The formylation takes place through the heating of a suspension of the amino carboxylic acid in formamide at temperatures of from 50 to 100° C. The N-formylation method is carried out in an inert atmosphere with high excess of formamide with conversions of 80-100%.

Furthermore, DD 230527 A discloses the formylation of aniline by formamide in the presence of formic acid or formic acid salts. The formanilide is obtained with conversions of more than 70%.

U.S. Pat. No. 3,347,916 describes the preparation of N-formyl compounds. The formylation of primary or secondary, aliphatic or aromatic, amines takes place by reacting the amine with formamide. The catalyst used is 10% by weight boric acid, based on formamide. The conversions, at 25-26%, based on formamide, are relatively low and the formylation product which forms has to be purified, which is costly.

There is a constant need for improved production methods for 4-formylaminopiperidine derivatives which permit simple reaction control and allow high conversions.

Furthermore, there is a need for methods with which the purest possible 4-formylaminopiperidine derivatives are accessible.

It was therefore an object of the present invention to develop a method for producing 4-formylaminopiperidine derivatives. It was a further object to make the production of 4-formylaminopiperidine derivatives possible without the use of potentially corrosive substances such as formic acid. It was a partial object to find a method with simple reaction control and high conversions. It was a further object of the invention to find a method which permits the production of the purest possible reaction products.

These and other objects are achieved, as is evident from the disclosure content of the present invention, by the various embodiments of the method according to the invention, which are described below.

Accordingly, a method for producing 4-formylaminopiperidine derivatives of the formula (I)

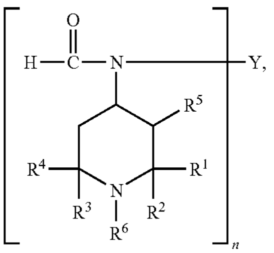

(I)

in which n is 1 or 2, $R^1$, $R^2$, $R^3$ and $R^4$, independently of one another, are identical or different and are $C_1$-$C_4$-alkyl or $R^1$ and $R^2$ or $R^3$ and $R^4$ together are a tetramethylene or pentamethylene group, $R^5$ is hydrogen or $C_1$-$C_4$-alkyl, $R^6$ is hydrogen, oxygen, $C_1$-$C_{22}$-alkyl, $C_3$-$C_{22}$-alkenyl, $C_1$-$C_{22}$-alkoxy, unsubstituted or substituted $C_7$-$C_{12}$-phenylalkyl, $C_1$-$C_{22}$-alkanoyl, $C_2$-$C_3$-cyanoalkyl, $C_1$-$C_{22}$-hydroxyalkyl or $C_2$-$C_{22}$-aminoalkyl and —if n=1—

Y is hydrogen, $C_1$-$C_{22}$-alkyl, $C_3$-$C_{22}$-alkenyl, $C_3$-$C_{12}$-cycloalkyl or bicycloalkyl, $C_2$-$C_{22}$-alkyl substituted by cyano, hydroxy or $C_1$-$C_4$-alkoxy, $C_4$-$C_{22}$-alkyl interrupted by ether oxygen, nitrogen or sulfur, unsubstituted or substituted $C_7$-$C_{22}$-phenyl or diphenylalkyl, unsubstituted or substituted phenyl, a radical of the formula

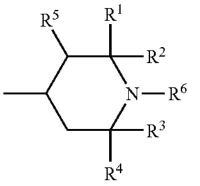

or $C_1$-$C_{22}$-alkyl comprising heterocyclic radicals, or

—when n=2—

Y is $C_2$-$C_{22}$-alkylene, $C_5$-$C_{22}$-cycloalkylene, $C_8$-$C_{14}$-phenylalkylene, phenylene or $C_4$-$C_{30}$-alkylene interrupted by ether oxygen, nitrogen, sulfur or 5- or 6-membered heterocycles, and also the acid addition salts of these compounds, has been found, where 4-aminopiperidine derivatives of the formula (II) or the acid addition salts of these compounds

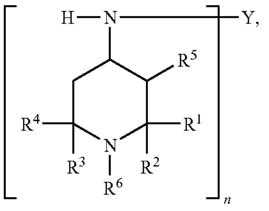

(II)

-continued (III)

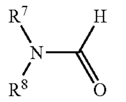

are reacted in the presence of compounds of the formula (III) where $R^7$, $R^8$, independently of one another, are identical or different and are hydrogen, $C_1$-$C_{22}$-alkyl, $C_3$-$C_{22}$-alkenyl, unsubstituted or substituted $C_7$-$C_{12}$-phenylalkyl, or $C_1$-$C_{22}$-alkanoyl.

For the purposes of this invention, expressions of the form $C_a$-$C_b$ refer to chemical compounds or substituents with a specific number of carbon atoms. The number of carbon atoms can be selected from the entire range from a to b, including a and b, a is at least 1 and b is always greater than a. The further specification of the chemical compounds or of the substituents takes place through expressions of the form $C_a$-$C_b$-V. V here is a chemical compound class or substituent class, for example alkyl compounds or alkyl substituents.

Halogen is fluorine, chlorine, bromine, or iodine, preferably fluorine, chlorine or bromine, particularly preferably fluorine or chlorine and specifically chlorine.

Specifically, the collective terms given for the various substituents have the following meanings:

$C_a$-$C_b$-Alkyl: straight-chain or branched hydrocarbon radicals having from a to b carbon atoms.

$C_1$-$C_4$-Alkyl: straight-chain or branched hydrocarbon radicals having up to 4 carbon atoms, for example $C_1$-$C_2$-alkyl or $C_3$-$C_4$-alkyl, preferably $C_1$-$C_2$-alkyl, for example methyl, ethyl, in particular methyl, or $C_3$-$C_4$-alkyl, propyl, isopropyl, n-butyl, sec-butyl, tert-butyl, 1,1-dimethylethyl.

$C_1$-$C_{22}$-Alkyl: straight-chain or branched hydrocarbon radicals having up to 22 carbon atoms, preferably $C_4$-$C_{22}$-alkyl, for example $C_1$-$C_{10}$-alkyl or $C_{11}$-$C_{22}$-alkyl, preferably $C_1$-$C_{10}$-alkyl, for example $C_1$-$C_3$-alkyl, such as methyl, ethyl, propyl, isopropyl, or $C_4$-$C_6$-alkyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, or $C_7$-$C_{10}$-alkyl, such as heptyl, octyl, 2-ethylhexyl, 2,4,4-trimethylpentyl, 1,1,3,3-tetramethylbutyl, nonyl or decyl, and isomers thereof.

$C_3$-$C_{22}$-Alkenyl: unsaturated, straight-chain or branched hydrocarbon radicals having 3 to 22 carbon atoms and a double bond in any desired position, for example $C_3$-$C_{10}$-alkenyl or $C_{11}$-$C_{22}$-alkenyl, preferably $C_3$-$C_{10}$-alkenyl, such as $C_3$-$C_4$-alkenyl, such as 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, or $C_5$-$C_6$-alkenyl, such as 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, and also $C_7$-$C_{10}$-alkenyl, such as the isomers of heptenyl, octenyl, nonenyl or decenyl.

$C_7$-$C_{12}$-Phenylalkyl: $C_1$-$C_6$-alkyl substituted with a phenyl radical and having in total 7 to 12 carbon atoms, for example $C_7$-$C_{10}$-phenylalkyl or $C_{11}$-$C_{12}$-phenylalkyl, preferably $C_7$-$C_{10}$-phenylalkyl, for example benzyl. Substituted $C_7$-$C_{12}$-phenylalkyls are additionally substituted on the phenyl ring.

$C_7$-$C_{22}$-Phenylalkyl or diphenylalkyl: $C_1$-$C_{16}$-alkyl substituted with one or two phenyl radicals or $C_1$-$C_{10}$-alkyl having in total 7 to 22 carbon atoms, for example $C_7$-$C_{10}$-phenylalkyl or $C_{13}$-$C_{16}$-diphenylalkyl or $C_{11}$-$C_{22}$-phenylalkyl or $C_{17}$-$C_{22}$-diphenylalkyl. Substituted $C_7$-$C_{22}$-phenylalkyls or diphenylalkyls are additionally substituted on one or both of the phenyl rings.

$C_1$-$C_{22}$-Alkanoyl: a straight-chain or branched alkyl group having 1 to 22 carbon atoms (as specified above), which are bound via a carbonyl group (—CO—), for example $C_1$-$C_{11}$-alkanoyl or $C_{12}$-$C_{22}$-alkanoyl, preferably $C_1$-$C_{11}$-alkanoyl, such as $C_1$-$C_5$-alkanoyl, such as acetyl, n- or isopropionyl, n-, iso-, sec- or tert-butanoyl, n-, iso-, sec- or tert-pentanoyl, or $C_9$-$C_{12}$-alkanoyl, such as n- or isononanoyl, or n-dodecanoyl.

$C_2$-$C_3$-Cyanoalkyl: $C_1$-$C_2$-alkyl having in total 2 to 3 carbon atoms and substituted with a CN group. For example 2-cyanoethyl.

$C_1$-$C_{22}$-Hydroxyalkyl: $C_1$-$C_{22}$-alkyl having 1 to 22 carbon atoms and substituted by a hydroxy group at any desired position.

$C_2$-$C_{22}$-Aminoalkyl: $C_1$-$C_{22}$-alkyl having 2 to 22 carbon atoms and substituted by an amino group at any desired position.

$C_3$-$C_{12}$-Cycloalkyl: monocyclic, saturated hydrocarbon groups having 3 to 12 carbon ring members, preferably $C_3$-$C_8$-cycloalkyl, such as cyclopropyl, cyclobutyl, cyclopentyl, cyclohexyl, cycloheptyl or cyclooctyl.

Bicycloalkyl: bicyclic, saturated or unsaturated hydrocarbon systems, such as, for example, norbornyl or norbenyl.

$C_1$-$C_{22}$-Alkoxy: is a straight-chain or branched alkyl group having 1 to 22 carbon atoms (as specified above), which are bound via an oxygen atom (—O—), for example $C_1$-$C_{10}$-alkoxy or $C_{11}$-$C_{22}$-alkoxy, preferably $C_1$-$C_{10}$-alkyloxy, particularly preferably $C_1$-$C_4$-alkoxy, such as, for example, methoxy, ethoxy, propoxy, butoxy.

$C_a$-$C_b$-Alkylene: straight-chain or branched hydrocarbon radicals with a to b carbon atoms.

$C_2$-$C_{22}$-Alkylene: straight-chain or branched hydrocarbon radicals having 2 to 22 carbon atoms, for example $C_2$-$C_{10}$-alkylene or $C_{11}$-$C_{22}$-alkylene, preferably $C_2$-$C_{10}$-alkylene, in particular tetramethylene, pentamethylene or hexamethylene.

$C_5$-$C_{22}$-Cycloalkylene: straight-chain or branched hydrocarbon radicals having 5 to 22 carbon atoms, comprising monocyclic, saturated hydrocarbon groups having 3 to 12 carbon ring members, preferably 5 to 8 carbon ring members.

$C_8$-$C_{14}$-Phenylalkylene: straight-chain or branched hydrocarbon radicals having 8 to 14 carbon atoms, comprising a phenylene group, where the hydrocarbon groups apart from the phenylene group are saturated.

Heterocycles: five- to twelve-membered, preferably five- to nine-membered, particularly preferably five- to six-membered ring systems having oxygen, nitrogen and/or sulfur atoms, if appropriate two or more rings, such as furyl, thiophenyl, pyrryl, pyridyl, indolyl, benzoxazolyl, dioxolyl, dioxyl, benzimidazolyl, benzthiazolyl, dimethylpyridyl, methyiquinolyl, dimethylpyrryl, methoxyfuryl, dimethoxypyridyl, difluoropyridyl, methylthiophenyl, isopropylthiophenyl or tert-butylthiophenyl. For example also piperidinyl, pyrrolidinyl.

5- or 6-membered heterocycles: 5- or 6-membered ring systems having oxygen, nitrogen and/or sulfur atoms, such as furyl, thiophenyl, pyrryl, pyridyl, piperidinyl, pyrrolidinyl.

In the course of the method according to the invention, the production of 4-formylaminopiperidine derivatives of the formula (I) and also of the acid addition salts of these compounds takes place by reacting 4-aminopiperidine derivatives of the formula (II) in the presence of compounds of the formula (III), preferably in the presence of dimethylformamide or formamide, in particular formamide. 4-Aminopiperidine derivatives of the formula (II) and 4-formylaminopiperidine derivatives of the formula (I) may be present and/or produced in the method according to the invention as acid addition salts of the particular compound. Naturally, using the method according to the invention, it is also possible to obtain mixtures of 4-formylaminopiperidine derivatives of the formula (I) by reacting mixtures of 4-aminopiperidine derivatives of the formula (II) in the presence of compounds of the formula (III). In the method according to the invention, preference is given to using pure formamide or a formamide solution in an inert solvent as compounds of the formula (III). Very particular preference is given to using pure formamide. The method according to the invention can naturally also be carried out with other use forms of the compounds of the formula (III) or of formamide, for example with suspensions or dispersions. The term compounds of the formula (III) is used by way of representation of all use forms of the compounds of the formula (III).

The production of 4-formylaminopiperidine derivatives of the formula (I) where n=2 preferably takes place from 4-aminopiperidine derivatives of the formula (II) where n=2. A by-product of the production is, for n=2, essentially only a small fraction of singly reacted monoamide. With the help of the method according to the invention, it is possible to obtain a monoamide fraction of less than 2 mol % based on the total conversion. Preferably, the monoamide fraction is less than 1.5 mol %. Through the method according to the invention, 4-formylaminopiperidine derivatives of the formula (I) where n=2 are therefore accessible in high purity.

Preferably, in the formula (I) and (II), $R^1$, $R^2$, $R^3$ and $R^4$, independently of one another, are identical or different and are $C_1$-$C_4$-alkyl. $R^1$, $R^2$, $R^3$ and $R^4$ are very preferably methyl.

$R^5$ is preferably hydrogen.

If $R^6$ is a substituted C7-C12-phenylalkyl, then the substituents are preferably $C_1$-$C_4$-alkyl, halogen, $C_1$-$C_4$-alkoxy, methylenedioxy, ethylenedioxy and/or di-$C_1$-$C_4$-alkylamino. Preferably, $R^6$ is hydrogen, $C_1$-$C_{22}$-alkyl or $C_3$-$C_{22}$-alkenyl. $R^6$ is particularly preferably hydrogen or $C_1$-$C_{22}$-alkyl and very particularly preferably $R^6$ is hydrogen. Surprisingly, it has been found that through the method according to the invention, if $R^6$ is hydrogen, a formylation takes place essentially only at the 4-amino position of the 4-aminopiperidine compound. The N—H group in the piperidine ring remains essentially unchanged.

If Y, when n=1, is a substituted $C_7$-$C_{12}$-phenyl or diphenylalkyl, then the substituents are preferably $C_1$-$C_4$-alkyl, halogen, $C_1$-$C_4$-alkoxy, methylenedioxy, ethylenedioxy and/or di-$C_1$-$C_4$-alkylamino. If Y, when n=1, is a substituted phenyl, then the substituents are preferably $C_1$-$C_4$-alkyl or $C_1$-$C_4$-alkoxy.

In the case of n=2 in the formulae (I) and (II), $R^1$, $R^2$, $R^3$, $R^4$, $R^6$ are very particularly preferably methyl, $R^5$ is hydrogen and Y is $C_6$-alkylene. The production of the 4-aminopiperidine derivatives of the formula (II) takes place in this preferred case by methods well known to the person skilled in the art, which are described, for example, in U.S. Pat. No. 4,331,586, EP 508 940, EP 302020, JP 07304737 and U.S. Pat. No. 4,605,743. For example, this production takes place by reductive alkylation of hexamethylenediamine in the presence of 2,2,6,6-tetramethyl-4-piperidone using hydrogenation catalysts such as Pd, Pt, Ni, Co in the presence of hydrogen either without a diluent or with the help of solvents. Analogously, many of the 4-aminopiperidine derivatives of the formula (II) can be obtained from the corresponding amines in conjunction with the 4-piperidones. Further production methods of the 4-aminopiperidine derivatives of the formula (II) are well known to the person skilled in the art from the prior art.

For the purposes of the method according to the invention, the reaction of 4-aminopiperidine derivatives of the formula (II) can take place in the presence of a solvent or "without a diluent". The reaction without a diluent means that essentially no solvents are present in the method according to the invention.

For the purposes of this invention, the term "solvent" is used by way of representation also for diluents. Dissolved substances are present in the solvent either in dissolved, suspended, dispersed or emulsified form. The term solvent also comprises solvent mixtures. Solvents are liquid under the reaction conditions of the method according to the invention. The term solvent does not comprise compounds of the formula (III).

The reaction without a diluent can preferably take place when 4-aminopiperidine derivatives of the formula (II) are soluble, suspendible, dispersible or emulsifiable in compounds of the formula (III) under the reaction conditions of the method according to the invention. According to the invention, the reaction can also take place without a diluent if 4-aminopiperidine derivatives of the formula (II) are liquid under the reaction conditions of the method according to the invention.

The amount of compounds of the formula (III) which can be used in the reaction without a diluent can vary over a large range, for example on account of the solubility of the 4-aminopiperidine derivatives of the formula (II) in compounds of the formula (III). In general, compounds of the formula (III) are used in from equimolar to fifteen-fold molar excess, based on the 4-aminopiperidine derivative of the formula (II). Preferably, in the course of the method according to the invention, a from equimolar to five-fold molar amount is used. The reaction without a diluent takes place preferably in a temperature range from 80° C. to 180° C. The reaction particularly preferably takes place in a range from 100° C. to 160° C. The reaction can be carried out at subatmospheric pressure, atmospheric pressure or superatmospheric pressure. Preferably, the reaction is carried out at atmospheric pressure or a slight superatmospheric pressure.

In one embodiment of the method according to the invention, a solvent, in particular an inert solvent, is used. Inert solvents are stable under the reaction conditions of the method according to the invention. This means the inert solvents do not decompose, do not react with themselves or starting materials or products of the conversion. In particular, inert solvents are stable toward compounds of the formula (III), amines, or ammonia. As solvents, preference is given to using aromatic organic hydrocarbons, for example toluene, xylene, dichlorobenzene, Solvesso™ 100, 150 or 200 (substituted aromatic mixtures). Very particular preference is given to using xylene or toluene as solvent. The amount of solvent used is dependent on the solubility of the feed materials and can vary within a wide range. Appropriate choice of the amount of solvent in the method according to the invention will avoid on the one hand undesired secondary effects, such as inadequate solubility of 4-aminopiperidine derivatives of the formula (II) if too little solvent is used, and on the other hand a greatly increased energy consumption for example for cooling or heating operations if too much solvent is used. In general, the amount of solvent is from 10 to 700% by weight, based on the amount of 4-aminopiperidine derivative of the formula (II). Preference is given to using from 10 to 500% by weight of solvent. 20 to 400% by weight of solvent are very preferably used.

The choice of reaction temperature depends on whether the method according to the invention takes place without a diluent or using a solvent. In one embodiment, the reaction temperature is dependent on the boiling point of the solvent or on the boiling range of the solvent mixture. In the method according to the invention, solvents with a boiling point lower than the boiling point of the 4-formylaminopiperidine derivative of the formula (I) are generally chosen. The reaction using a solvent generally takes place in a temperature range from 100° C. to 180° C. Preferably, the reaction takes place in a range from 120° C. to 160° C. The reaction can be carried out at subatmospheric pressure, atmospheric pressure or at a slight superatmospheric pressure.

The duration of the method according to the invention until essentially complete conversion is achieved can vary within a wide range depending on the particular feed materials and the reaction conditions. The duration of the method according to the invention is, for example, from 1 to 48 hours. Preferably, the duration of the method according to the invention is less than 24 hours.

In one embodiment of the method according to the invention, the reaction takes place in the presence of at least one protic acid or at least one Lewis acid. The use of mixtures of protic acids or mixtures of Lewis acids and also mixtures of protic acids and Lewis acids is naturally likewise possible. In general, the reaction rate of the conversion increases in the presence of at least one protic acid or Lewis acid, that means protic or Lewis acids act as catalysts.

In general, any desired protic or Lewis acids can be used in the method according to the invention. The protic acids used are organic carboxylic acids, such as acetic acid or propionic acid, or mineral acids, such as hydrochloric acid, nitric acid or sulfuric acid. Preference is given to less corrosive protic acids such as, for example, acetic acid. The Lewis acids used are boric acid or zinc salt, such as zinc acetate or zinc chloride. Preferably, boric acid is used as Lewis acid. The concentration of the protic or Lewis acid can vary within wide ranges. Preferably, the concentration of the protic acid is from 4% by weight to 40% by weight, based on 4-aminopiperidine derivative of the formula (II). The concentration range is particularly preferably from 4% by weight to 20% by weight. Very particularly preferably from 5% by weight to 10% by weight. The concentration of the Lewis acid is preferably from 0.1% by weight to 2.5% by weight, based on 4-aminopiperidine derivative of the formula (II). The concentration range is particularly preferably from 0.2% by weight to 1.2% by weight. Very particularly preferably from 0.3% by weight to 1.0% by weight.

In one preferred embodiment of the method according to the invention, the reaction takes place in the presence of at least one protic or Lewis acid in the concentration ranges stated above.

In a further preferred embodiment of the method according to the invention, the reaction takes place in the presence of at least one protic acid and at least one Lewis acid in the concentration ranges stated above.

In a preferred embodiment, the method according to the invention takes place in xylene as solvent in the presence of acetic acid (glacial acetic) and boric acid as catalyst.

In one embodiment, the reaction in the course of the method according to the invention takes place at a water content of less than 1% by weight, based on the 4-aminopiperidine derivatives of the formula (II). Preferably, the water content is less than 0.5% by weight. Processing is very preferably essentially water-free. In one embodiment of the method according to the invention, the feed materials are purified such that the water content overall, based on the 4-aminopiperidine derivatives of the formula (II), is less than 1% by weight. For example, it is to be taken into consideration that compounds of the formula (III) are often hygroscopic. If the water content exceeds the required limiting values, then the compounds of the formula (III) are purified prior to use. Purification generally takes place by methods known to a person skilled in the art, for example by distillation. Furthermore, the water content of the solvent is to be established prior to use and, if appropriate, if excessive is to be dealt with as in the case of the compounds of the formula (III). The optional further substances such as protic acids or Lewis acids are dealt with analogously. As a result of the low water content, the method according to the invention permits high purity of the products coupled with a simultaneous high conversion.

In one embodiment, the reaction in the course of the method according to the invention takes place essentially with the exclusion of oxygen. The exclusion of oxygen is achieved by methods known generally to the person skilled in the art. For example, the apparatus in which the method according to the invention is carried out is flushed before the start of the reaction with an inert gas, for example nitrogen, in order to displace oxygen. The reaction preferably takes place under a slight nitrogen superatmospheric pressure. For example, the nitrogen superatmospheric pressure is from 5 to 50 mbar. Preferably, the nitrogen superatmospheric pressure is from 10 to 40 mbar.

In another embodiment, the method according to the invention for producing 4-formylaminopiperidine derivatives of the formula (I) generally consists of one or more process steps, which can proceed consecutively or even at the same time. For example, the method according to the invention comprises the following process steps: synthesis of 4-formylaminopiperidine derivatives of the formula (I) by reacting 4-aminopiperidine derivatives of the formula (II) in the presence of compounds of the formula (III), optionally removal of the excess compounds of the formula (III), optionally the separating off of a solvent and of a 4-formylaminopiperidine derivative of the formula (I), optionally the isolation of a 4-formylaminopiperidine derivative of the formula (I), optionally the work-up of a 4-formylaminopiperidine derivative of the formula (I). These steps preferably take place consecutively in the order: synthesis, optional removal, optional separation, optional isolation, and optional work-up.

Following completion of the reaction, i.e. essentially complete completion of the synthesis in the course of the method according to the invention, excess compounds of the formula (III) can, if appropriate, be removed.

In a preferred embodiment of the method according to the invention, excess compounds of the formula (III), if present, are deactivated. The optional deactivation generally takes place by hydrolysis. The hydrolysis can take place, for example, with the help of water and/or aqueous alkaline solutions or aqueous acids. The hydrolysis preferably takes place with aqueous alkali metal or alkaline earth metal hydroxide solutions. The hydrolysis is very particularly preferably carried out in the presence of aqueous sodium hydroxide solution.

In a further preferred embodiment of the method according to the invention, excess compounds of the formula (III), if present, are removed by distillation.

However, removal of the excess compounds of the formula (III), for example by deactivation or distillation, can be dispensed with entirely as a process step.

In one embodiment of the method according to the invention, following the optional deactivation of the excess compounds of the formula (III), the solvent, if present, is separated off. The solvent is generally separated off in a manner well known to the person skilled in the art. Preferably, separation can take place by distillation. The solvent is very preferably separated off by azeotropic steam distillation. The solvent can be used again after work-up. Residual water is preferably separated off before reutilizing the solvent.

In one embodiment, the solvent, in particular xylene, following completed reaction and hydrolysis of excess compounds of the formula (III), optionally after adding water, is azeotropically distilled off and reutilized. Residual water is preferably removed azeotropically before reutilizing the solvent, in particular xylene.

Following the optional deactivation of the excess compounds of the formula (III) and the optional removal of the solvent, in the course of the method according to the invention, optional isolation of the 4-formylaminopiperidine derivatives of the formula (I) from the rest of the reaction mixture takes place. The term reaction mixture comprises the substance mixtures which arise during the individual process steps of the method according to the invention. For example, reaction mixture refers to a mixture of starting materials, products, solvents, and catalysts. In particular, the term reaction mixture also comprises solids precipitated out in the method according to the invention in contact with the solvent and the compounds still dissolved in the solvent.

In a preferred embodiment of the method according to the invention, during the isolation, the 4-formylaminopiperidine derivative of the formula (I) is removed by distillation from the reaction mixture.

In another preferred embodiment of the method according to the invention, the 4-formylaminopiperidine derivative of the formula (I) is separated off from an aqueous phase because of lack of solubility. An aqueous phase is formed while carrying out the method according to the invention for example via the hydrolysis of compounds of the formula (III) with the help of aqueous alkaline solutions and optionally also while separating off the solvent by azeotropic steam distillation. However, the aqueous phase can also be produced in other ways, for example by adding water or essentially aqueous solutions to the reaction mixture. Isolation of the 4-formylpiperidine derivative of the formula (I) from the aqueous phase preferably takes place by crystallization. The aqueous phase is referred to in this case as mother liquor.

In the course of a number of embodiments of the method according to the invention, the isolation, for example the crystallization, can be accelerated or improved by using increased amounts of water in the hydrolysis or by adding a solvent, for example xylene, after the reaction, but before the start of the deactivation, for example by hydrolysis.

The further optional work-up of the 4-formylpiperidine derivative of the formula (I) generally takes place in the course of the method according to the invention in accordance with techniques well known to the person skilled in the art. By way of example, a sequence of filtration, washing and drying steps may be described here. Alternatively to this, for example, a sequence of centrifugation, washing and drying steps can be carried out. In the case of liquid products, isolation and work-up takes place, for example, by customary distillation steps well known to the person skilled in the art.

In one embodiment of the method according to the invention, the reaction mixture is subjected to a filtration following the reaction. The filtration can consist of one or more filtration steps and the 4-formylaminopiperidine derivative of the formula (I) remains in the solid filtration residue. In order to ensure higher purity of the 4-formylpiperidine derivative of the formula (I) by the method according to the invention, one or more washing step(s) generally follows the filtration step. The filtration residue is preferably washed with water. However, in the course of the method according to the invention, isolation and work-up of the 4-formylpiperidine derivative of the formula (I) can also be carried out by other techniques.

In another embodiment of the method according to the invention, a liquid additive or an additive suspended, emulsified or dissolved in an inert solvent is added to the reaction mixture.

The addition of the additive to the reaction mixture can in principle take place at any desired time, for example before, during and/or after the reaction according to the invention of 4-aminopiperidine derivatives of the formula (II). Preferably, this addition takes place during and/or after the reaction. Very preferably, the addition of a liquid additive or an additive suspended, emulsified or dissolved in an inert solvent takes place after the reaction.

Preferably, the additive is added in an amount of from 0.01 to 1.5% by weight, particularly preferably from 0.01 to 0.75% by weight, very particularly preferably from 0.01 to 0.25% by weight. The additive is preferably an additive from the class of plastics additives, as described, for example, in the "Plastics Additives Handbook", Verlag Carl Hanser, ISBN 978-3-446-19579-0. The plastics additive is particularly preferably a compound from the class of antioxidants, metal deactivators, further photostabilizers, plasticizers, lubricants, flame retardants, antistats, optical brighteners or colorants. The plastics additive is very preferably a white oil, such as, for example, Pionier® 2071 or 1115 (Pionier, CAS 8042-47-5), Tudalen® 3036 (CAS 64741-89-5) or Winog® 70 (H&R, CAS 8012-95-1), Enerpar® M006 or M002 (BP, CAS 8042-47-5), Primol® 382 (Exxon Mobile, CAS 8012-95-1), Ondina Oil G17 (Esso, CAS 8042-47-5).

The method according to the invention can be carried out in any desired apparatuses which permit execution of the (optional) process steps. The apparatuses for carrying out for example: the synthesis of 4-formylaminopiperidine derivatives of the formula (I) by reacting 4-aminopiperidine derivatives of the formula (II) in the presence of compounds of the formula (III), the optional deactivation of the excess compounds of the formula (III), the optional removal of a solvent and of a 4-formylaminopiperidine derivative of the formula (I), the optional isolation of as 4-formylaminopiperidine derivative of the formula (I), or the optional work-up of a 4-formylaminopiperidine derivative of the formula (I), are generally well known to the person skilled in the art.

The 4-formylaminopiperidine derivatives produced according to the invention can be used for protecting inanimate organic material against the effect of light, in particular as photostabilizers against the harmful effect of UV radiation. For example, they are used as photostabilizers for polymers. Polymers here is to be understood as meaning any desired plastics, preferably thermoplastics, in particular films, fibers or moldings of any desired shape. The polymers are, for example, polyolefins, polyamides, polystyrenes, polyacrylonitriles, polycarbonates, acrylonitrile-butadiene-styrenes (ABS), polyvinyl chlorides, polyurethanes, or polyesters. Polymers can also be copolymers, mixtures or blends of the abovementioned polymers. Preferred polymers are polyolefins, in particular polyethylene or polypropylene. Further preferred polymers are polystyrenes or ABS. Likewise preferred polymers are polyamides.

The method according to the invention permits the production of 4-formylaminopiperidine derivatives. In the course of the method according to the invention, the use of corrosive substances such as formic acid can be avoided. The method according to the invention is notable for simple reaction control with which 4-formylaminopiperidine derivatives are accessible in high purity with high conversions.

The above embodiments of the method according to the invention and the examples below illustrate the present invention by way of example. However, many other variations of the method and combinations of the features of the method according to the invention are conceivable for the person skilled in the art without departing from the scope of the patent claims.

EXAMPLES

The purity of the products was determined using gas chromatography.

Example 1

Preparation of N,N'-1,6-hexanediylbis[N-(2,2,6,6-tetramethyl-4-piperidinyl)formamide with Solvent: Xylene 40 ml of formamide, 170 g of N,N'-bis(2,2,6,6-tetramethyl-4-piperidinyl)-1,6-hexanediamine and 0.9 g of boric acid are added to 60 ml of xylene. 20 ml of acetic acid are added and the mixture is heated under an inert gas atmosphere to reflux temperature. After a reaction time of about 10 hours, the reaction mixture is cooled to approximately 90 to 95° C., and 40 ml of water is allowed to run in with stirring. Then, with further stirring, sufficient aqueous sodium hydroxide solution is added to deactivate the excess formamide. The reaction mixture is again brought to the boil and xylene is distilled of azeotropically. The mixture is then cooled to approximately 60° C., water is added again, and the resulting solid product residue is separated off. The product residue is subsequently washed with water and then dried. Drying gives about 185 g of product (95% yield) in a purity greater than 99%. The melting point of the product is 157-158° C.

Example 2

Preparation of N,N'-1,6-hexanediylbis[N-(2,2,6,6-tetramethyl-4-piperidinyl)-formamide without Solvent 25 g of acetic acid, 0.5 g of boric acid, 157 g of N,N'-bis (2,2,6,6-tetramethyl-4-piperidinyl)-1,6-hexanediamine are added to 72 g of formamide and stirred for about 6 hours at approximately 160° C. Under reflux and evaporative cooling, 150 ml of water and sufficient aqueous sodium hydroxide solution to deactivate the excess formamide are added and the mixture is stirred for a further 2 hours at approximately 95° C., during which the product finely crystallizes out. After cooling to room temperature, the product residue is separated off and washed with water. This gives the product in a purity of 99.6% and with a yield of 89%.

Example 3

Preparation of N-cyclohexyl-N-(2,2,6,6-tetramethylpiperidin-4-yl)formamide 19.1 g of N-cyclohexyl-N-2,2,6,6-tetramethylpiperidine are admixed with 50 g of formamide, 0.12 g of boric acid and 1 ml of acetic acid and stirred under an inert gas atmosphere for about 12 hours at approximately 160° C. Then, at approximately 100° C., 50 ml of water are added and, over the course of one hour, sufficient aqueous sodium hydroxide solution to deactivate the excess formamide is added and the mixture is afterstirred for one hour at approximately 90° C. After cooling to room temperature, the product residue is separated off and dried. 11.5 g of the colorless product with a purity of 99.8% are obtained.

Example 4

Preparation of N-butyl, 2,2,6,6-tetramethyl-4-piperidineamineformamide 43.4 g of N-butyl, 2,2,6,6-tetramethyl-4-piperidineamine, 100 ml of xylene, 18 g of formamide, 1 g of boric acid and 10 g of acetic acid are stirred for about 6 hours under an inert gas atmosphere at reflux. After cooling to room temperature, two phases are obtained which are distilled in vacuo. The product passes over at 180-182° C./21 mbar. 45 g (92%) of a clear liquid with a purity of 99.5% are obtained.

Example 5

25 g of acetic acid, 0.5 g of boric acid, 157 g of N,N'-bis (2,2,6,6-tetramethyl-4-piperidinyl)-1,6-hexanediamine are added to 72 g of formamide and the mixture is stirred for 8.5 hours at approximately 160° C. Then, 0.3% by weight, based on the product, of mineral white oil Pionier® 2071 is added. Under reflux and evaporative cooling, 150 ml of water and sufficient aqueous sodium hydroxide solution to deactivate the excess formamide are added dropwise and the mixture is stirred for a further 2 hours at approximately 95° C., during which the product finely crystallizes out. After cooling to room temperature, the product residue is separated off and washed with water. The product is obtained in a purity of 99.6% and with a yield of 96.5%.

Example 6

40 ml of formamide and 170 g of N,N'-bis(2,2,6,6-tetramethyl-4-piperidinyl)-1,6-hexanediamine are added to 60 ml of xylene. 20 ml of acetic acid are added and the mixture is heated to reflux temperature under an inert gas atmosphere. After a reaction time of about 10 hours, the reaction mixture is cooled to approximately 90 to 95° C., and 40 ml of water are allowed to run in with stirring. Then, with further stirring, sufficient aqueous sodium hydroxide solution to deactivate the excess formamide is added. The reaction mixture is again brought to the boil and xylene is distilled off azeotropically. Then, the mixture is cooled to approximately 60° C., water is added again, and the resulting solid product residue is separated off. The product residue is thoroughly washed with water and then dried. Drying gives the product in 94.5% yield in a purity of 99.9%.

The invention claimed is:

1. A method for producing a 4-formylaminopiperidine compound of formula (I)

(I)

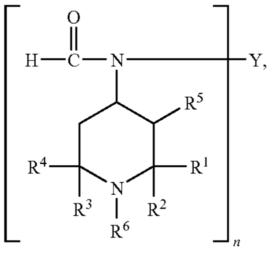

in which n is 1 or 2, $R^1$, $R^2$, $R^3$ and $R^4$, independently of one another, are identical or different and are $C_1$-$C_4$-alkyl or $R^1$ and $R^2$ or $R^3$ and $R^4$ together are a tetramethylene or pentamethylene group, $R^5$ is hydrogen or $C_1$-$C_4$-alkyl, $R^6$ is hydrogen, oxygen, $C_1$-$C_{22}$-alkyl, $C_3$-$C_{22}$-alkenyl, $C_1$-$C_{22}$-alkoxy, unsubstituted or substituted $C_7$-$C_{12}$-phenylalkyl, $C_1$-$C_{22}$-alkanoyl, $C_2$-$C_3$-cyanoalkyl, $C_1$-$C_{22}$-hydroxyalkyl or $C_2$-$C_{22}$-aminoalkyl and —if n=1—

Y is hydrogen, $C_1$-$C_{22}$-alkyl, $C_3$-$C_{22}$-alkenyl, $C_3$-$C_{12}$-cycloalkyl or bicycloalkyl, $C_2$-$C_{22}$-alkyl substituted by cyano, hydroxy or $C_1$-$C_4$-alkoxy, $C_4$-$C_{22}$-alkyl interrupted by ether oxygen, nitrogen or sulfur, unsubstituted or substituted $C_7$-$C_{22}$-phenyl or diphenylalkyl, unsubstituted or substituted phenyl, a radical of formula

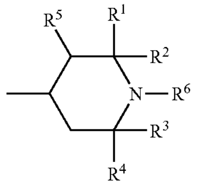

or $C_1$-$C_{22}$-alkyl comprising a heterocyclic radical, or

—when n=2—

Y is $C_2$-$C_{22}$-alkylene, $C_5$-$C_{22}$-cycloalkylene, $C_8$-$C_{14}$-phenylalkylene, phenylene or $C_4$-$C_{30}$-alkylene interrupted by ether oxygen, nitrogen, sulfur or 5- or 6-membered heterocycles, and also an acid addition salt thereof, comprising reacting a 4-aminopiperidine compound of formula (II) or an acid addition salt thereof (II)

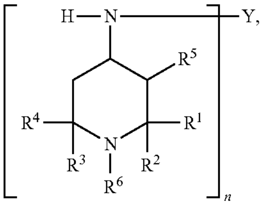

in the presence of a compound of formula (III)

(III)

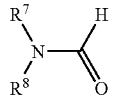

wherein $R^7$, $R^8$, independently of one another, are identical or different and are hydrogen, $C_1$-$C_{22}$-alkyl, $C_3$-$C_{22}$-alkenyl, unsubstituted or substituted $C_7$-$C_{12}$-phenylalkyl, or $C_1$-$C_{22}$-alkanoyl, and the reaction takes place in the presence of at least one protic acid and at least one Lewis acid.

2. The method according to claim 1, wherein the reaction takes place in the presence of a solvent inert toward the compound of formula (III), amine, or ammonia.

3. The method according to claim 1, wherein the reaction takes place without the presence of a solvent.

4. The method according to claim 2, wherein the solvent is an aromatic organic hydrocarbon.

5. The method according to claim 1, wherein oxygen remains essentially excluded during the reaction.

6. The method according to claim 1, wherein processing is essentially water-free during the reaction.

7. The method according to claim 1, wherein, after the reaction of the 4-aminopiperidine compound of formula (II) is complete, excess compound of formula (III) is deactivated.

8. The method according to claim 1, wherein, after the reaction of the 4-aminopiperidine compound of formula (II) is complete, excess compound of formula (III) is removed by distillation.

9. A method for separating off the 4-formylaminopiperidine compound of formula (I) produced according to claim 2, wherein, following the addition of water, the solvent is distilled off azeotropically.

10. The method according to claim 1, wherein additionally a liquid additive or an additive suspended, emulsified or dissolved in a solvent inert is added to the reaction mixture.

11. The method according to claim 10, wherein the additive is an additive from the class of plastics additives.

12. The method according to claim 11, wherein the additive is a compound selected from the group consisting of an antioxidant, a metal deactivator, a photoprotective agent, a plasticizer, a lubricant, a flame retardant, a antistat, an optical brightener and a colorant.

13. The method according to claim 1, wherein the reaction takes place in the presence of acetic acid and boric acid.

14. A method for separating off the 4-formylaminopiperidine compound of formula (I) produced according to claim 5, wherein, following the addition of water, the solvent is distilled off azeotropically.

15. A method for separating off the 4-formylaminopiperidine compound of formula (I) produced according to claim 6, wherein, following the addition of water, the solvent is distilled off azeotropically.

16. The method according to claim 2, wherein additionally a liquid additive or an additive suspended, emulsified or dissolved in a solvent inert is added to the reaction mixture.

17. The method according to claim 5, wherein the reaction takes place under a nitrogen superatmosphere pressure of from 5 to 50 mbar.

18. The method according to claim 6, wherein the water content is less than 1% by weight, based on the 4-aminopiperidine compounds of formula (II).

* * * * *